(12) United States Patent
Hall et al.

(10) Patent No.: US 11,179,543 B2
(45) Date of Patent: Nov. 23, 2021

(54) RELEASABLE CONDUIT CONNECTORS

(71) Applicant: Merit Medical Systems, Inc., South Jordan, UT (US)

(72) Inventors: John Hall, North Salt Lake, UT (US); Wayne Mower, Bountiful, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 500 days.

(21) Appl. No.: 16/033,515

(22) Filed: Jul. 12, 2018

(65) Prior Publication Data

US 2019/0015627 A1 Jan. 17, 2019

Related U.S. Application Data

(60) Provisional application No. 62/532,577, filed on Jul. 14, 2017.

(51) Int. Cl.
*A61M 25/00* (2006.01)
*A61M 39/04* (2006.01)
(Continued)

(52) U.S. Cl.
CPC ...... *A61M 25/0026* (2013.01); *A61M 1/3653* (2013.01); *A61M 25/0043* (2013.01); *A61M 25/09* (2013.01); *A61M 39/0247* (2013.01); *A61M 39/04* (2013.01); *A61M 39/105* (2013.01); *A61M 39/1011* (2013.01); *A61M 25/0045* (2013.01); *A61M 2025/0034* (2013.01); *A61M 2025/0059* (2013.01);
(Continued)

(58) Field of Classification Search
CPC ............... A61M 1/3653; A61M 39/04; A61M 39/0247; A61M 25/0043; A61M 2025/0034; A61M 2039/0258; A61M 39/1011
See application file for complete search history.

(56) References Cited

U.S. PATENT DOCUMENTS 3,357,432 A 12/1967 Sparks
3,435,823 A 4/1969 Edwards
(Continued)

FOREIGN PATENT DOCUMENTS

DE 4418910 12/1995
DE 29515546 3/1997
(Continued)

OTHER PUBLICATIONS

Office Action dated Aug. 21, 2019 for U.S. Appl. No. 14/192,567.
(Continued)

*Primary Examiner* — Leslie R Deak
(74) *Attorney, Agent, or Firm* — Stoel Rives LLP

(57) ABSTRACT

Systems and methods of implanting a vascular access technologies and declotting vascular access technologies, such as vascular access assemblies that facilitate hemodialysis, are provided. The methods can include disposing a first tubular conduit within a patient to access a vascular access assembly within the heart of the patient. The first tubular conduit can be coupled to the vascular access assembly such that the first tubular conduit can be decoupled from the vascular access assembly to evacuate a clot within the vascular access assembly, and then recouple the first tubular conduit to the vascular access assembly.

9 Claims, 11 Drawing Sheets

(51) Int. Cl.
  *A61M 39/02* (2006.01)
  *A61M 39/10* (2006.01)
  *A61M 1/36* (2006.01)
  *A61M 25/09* (2006.01)
  *A61M 39/00* (2006.01)

(52) U.S. Cl.
  CPC .......... *A61M 2025/091* (2013.01); *A61M 2039/0018* (2013.01); *A61M 2039/0258* (2013.01)

(56) References Cited

U.S. PATENT DOCUMENTS

| | | |
|---|---|---|
| 3,490,438 A | 1/1970 | Lavender et al. |
| 3,683,926 A | 8/1972 | Suzuki |
| 3,814,137 A | 6/1974 | Martinez |
| 3,818,511 A | 6/1974 | Goldberg et al. |
| 3,826,257 A | 7/1974 | Buselmeier |
| 3,853,126 A | 12/1974 | Schulte |
| 3,882,862 A | 5/1975 | Berend |
| 3,998,222 A | 12/1976 | Shihata |
| 4,076,023 A | 2/1978 | Martinez |
| 4,133,312 A | 1/1979 | Burd |
| 4,184,489 A | 1/1980 | Burd |
| 4,214,586 A | 7/1980 | Mericle |
| 4,318,401 A | 3/1982 | Zimmerman |
| 4,366,819 A | 1/1983 | Kaster |
| 4,427,219 A | 1/1984 | Madej |
| 4,441,215 A | 4/1984 | Kaster |
| 4,447,237 A | 5/1984 | Frisch et al. |
| 4,496,349 A | 1/1985 | Cosentino |
| 4,496,350 A | 1/1985 | Cosentino |
| 4,503,568 A | 3/1985 | Madras |
| 4,517,747 A | 5/1985 | Morin |
| 4,550,447 A | 11/1985 | Seiler, Jr. |
| 4,619,641 A | 10/1986 | Schanzer |
| 4,655,771 A | 4/1987 | Wallsten |
| 4,723,948 A | 2/1988 | Clark et al. |
| 4,734,094 A | 3/1988 | Jacob et al. |
| 4,753,236 A | 6/1988 | Healy |
| 4,771,777 A | 9/1988 | Horzewski et al. |
| 4,772,268 A | 9/1988 | Bates |
| 4,786,345 A | 11/1988 | Wood |
| 4,790,826 A | 12/1988 | Elftman |
| 4,822,341 A | 4/1989 | Colone |
| 4,848,343 A | 7/1989 | Wallsten et al. |
| 4,850,999 A | 7/1989 | Planck |
| 4,877,661 A | 10/1989 | House et al. |
| 4,898,591 A | 2/1990 | Jang et al. |
| 4,898,669 A | 2/1990 | Tesio |
| 4,917,087 A | 4/1990 | Walsh et al. |
| 4,919,127 A | 4/1990 | Pell |
| 4,929,236 A | 5/1990 | Sampson |
| 4,955,899 A | 9/1990 | Della Corna et al. |
| 5,026,513 A | 6/1991 | House et al. |
| 5,041,098 A | 8/1991 | Loiterman et al. |
| 5,042,161 A | 8/1991 | Hodge |
| 5,053,023 A | 10/1991 | Martin |
| 5,061,275 A | 10/1991 | Wallsten et al. |
| 5,061,276 A | 10/1991 | Tu et al. |
| 5,064,435 A | 11/1991 | Porter |
| 5,104,402 A | 4/1992 | Melbin |
| 5,171,227 A | 12/1992 | Twardowski et al. |
| 5,171,305 A | 12/1992 | Schickling et al. |
| 5,192,289 A | 3/1993 | Jessen |
| 5,192,310 A | 3/1993 | Herweck et al. |
| 5,197,976 A | 3/1993 | Herweck et al. |
| 5,251,642 A | 10/1993 | Handlos |
| 5,282,860 A | 2/1994 | Matsuno et al. |
| 5,330,500 A | 7/1994 | Song |
| 5,336,616 A | 8/1994 | Livesey et al. |
| 5,353,513 A | 10/1994 | Round |
| 5,399,168 A | 3/1995 | Wadsworth |
| 5,405,320 A | 4/1995 | Twardowski et al. |
| 5,405,339 A | 4/1995 | Kohnen et al. |
| 5,454,790 A | 10/1995 | Dubrul |
| 5,474,268 A | 12/1995 | Yu |
| 5,474,563 A | 12/1995 | Myler et al. |
| 5,476,451 A | 12/1995 | Ensminger et al. |
| 5,496,294 A | 3/1996 | Hergenrother et al. |
| 5,509,897 A | 4/1996 | Twardowski et al. |
| 5,549,663 A | 8/1996 | Cottone, Jr. |
| 5,558,641 A | 9/1996 | Glantz et al. |
| 5,562,617 A | 10/1996 | Finch, Jr. et al. |
| 5,562,618 A | 10/1996 | Cai et al. |
| 5,591,226 A | 1/1997 | Trerotola et al. |
| 5,607,463 A | 3/1997 | Schwartz et al. |
| 5,624,413 A | 4/1997 | Markel et al. |
| 5,637,088 A | 6/1997 | Wenner et al. |
| 5,637,102 A | 6/1997 | Tolkoff et al. |
| 5,645,532 A | 7/1997 | Horgan |
| 5,647,855 A | 7/1997 | Frooskin |
| 5,669,637 A | 9/1997 | Chitty et al. |
| 5,669,881 A | 9/1997 | Dunshee |
| 5,674,272 A | 10/1997 | Bush et al. |
| 5,676,346 A | 10/1997 | Leinsing |
| 5,743,894 A | 4/1998 | Swisher |
| 5,755,773 A | 5/1998 | Schuster |
| 5,755,775 A | 5/1998 | Trerotola et al. |
| 5,792,104 A | 8/1998 | Speckman et al. |
| 5,797,879 A | 8/1998 | Decampli |
| 5,800,512 A | 9/1998 | Lentz et al. |
| 5,800,514 A | 9/1998 | Nunez et al. |
| 5,800,522 A | 9/1998 | Campbell |
| 5,810,870 A | 9/1998 | Myers et al. |
| 5,830,224 A | 11/1998 | Cohn et al. |
| 5,840,240 A | 11/1998 | Stenoien et al. |
| 5,866,217 A | 2/1999 | Stenoien et al. |
| 5,904,967 A | 5/1999 | Ezaki et al. |
| 5,931,829 A | 8/1999 | Burbank et al. |
| 5,931,865 A | 8/1999 | Silverman et al. |
| 5,957,974 A | 9/1999 | Thompson et al. |
| 5,997,562 A | 12/1999 | Zadno-Azizi |
| 6,001,125 A | 12/1999 | Golds et al. |
| 6,019,788 A | 2/2000 | Butters et al. |
| 6,036,724 A | 3/2000 | Lentz et al. |
| 6,102,884 A | 8/2000 | Squitieri |
| 6,156,016 A | 12/2000 | Maginot |
| 6,167,765 B1 | 1/2001 | Weitzel |
| 6,171,295 B1 | 1/2001 | Garabedian |
| 6,231,085 B1 | 5/2001 | Olson |
| 6,245,098 B1 | 6/2001 | Feeser |
| 6,255,396 B1 | 7/2001 | Ding et al. |
| 6,261,255 B1 | 7/2001 | Mullis et al. |
| 6,261,257 B1 | 7/2001 | Uflacker et al. |
| 6,280,466 B1 | 8/2001 | Kugler et al. |
| 6,308,992 B1 | 10/2001 | Mitsui et al. |
| 6,309,411 B1 | 10/2001 | Lashinski et al. |
| 6,319,279 B1 | 11/2001 | Shannon et al. |
| 6,338,724 B1 | 1/2002 | Dossa |
| 6,398,764 B1 | 6/2002 | Finch, Jr. et al. |
| 6,402,767 B1 | 6/2002 | Nash et al. |
| 6,428,571 B1 | 8/2002 | Lentz et al. |
| 6,436,132 B1 | 8/2002 | Patel et al. |
| 6,582,409 B1 | 6/2003 | Squitieri |
| 6,585,762 B1 | 7/2003 | Stanish |
| 6,610,004 B2 | 8/2003 | Viole et al. |
| 6,689,096 B1 | 2/2004 | Loubens et al. |
| 6,689,157 B2 | 2/2004 | Madrid et al. |
| 6,692,461 B2 | 2/2004 | Wantink |
| 6,699,233 B2 | 3/2004 | Slanda et al. |
| 6,702,748 B1 | 3/2004 | Nita et al. |
| 6,702,781 B1 | 3/2004 | Reifart et al. |
| 6,706,025 B2 | 3/2004 | Engelson et al. |
| 6,719,781 B1 | 4/2004 | Kim |
| 6,719,783 B2 | 4/2004 | Lentz et al. |
| 6,730,096 B2 | 5/2004 | Basta |
| 6,733,459 B1 | 5/2004 | Atsumi |
| 6,740,273 B2 | 5/2004 | Lee |
| 6,749,574 B2 | 6/2004 | O'Keefe |
| 6,752,826 B2 | 6/2004 | Holloway et al. |
| 6,758,836 B2 | 7/2004 | Zawacki |
| 6,858,019 B2 | 2/2005 | McGuckin, Jr. et al. |
| 6,926,724 B1 | 8/2005 | Chu |

(56) References Cited

U.S. PATENT DOCUMENTS

| | | | |
|---|---|---|---|
| 6,926,735 B2 | 8/2005 | Henderson | |
| 6,976,952 B1 | 12/2005 | Maini et al. | |
| 6,981,987 B2 | 1/2006 | Huxel et al. | |
| 7,011,645 B2 | 3/2006 | McGuckin, Jr. et al. | |
| 7,025,741 B2 | 4/2006 | Cull | |
| 7,036,599 B2 | 5/2006 | Matteucci | |
| 7,044,937 B1 | 5/2006 | Kirwan et al. | |
| 7,101,356 B2 | 9/2006 | Miller | |
| 7,131,959 B2 | 11/2006 | Blatter | |
| 7,211,074 B2 | 5/2007 | Sansoucy | |
| 7,244,271 B2 | 7/2007 | Lenz et al. | |
| 7,244,272 B2 | 7/2007 | Dubson et al. | |
| 7,252,649 B2 | 8/2007 | Sherry | |
| 7,297,158 B2 | 11/2007 | Jensen | |
| 7,351,257 B2 | 4/2008 | Kaldany | |
| 7,399,296 B2 | 7/2008 | Poole et al. | |
| 7,438,699 B2 | 10/2008 | Pecor et al. | |
| 7,452,374 B2 | 11/2008 | Hain et al. | |
| 7,507,229 B2 | 3/2009 | Hewitt et al. | |
| 7,588,551 B2 | 9/2009 | Gertner | |
| 7,708,722 B2 | 5/2010 | Glenn | |
| 7,722,665 B2 | 5/2010 | Anwar et al. | |
| RE41,448 E | 7/2010 | Squitieri | |
| 7,762,977 B2 * | 7/2010 | Porter | A61M 1/3655 604/6.16 |
| 7,789,908 B2 | 9/2010 | Sowinski et al. | |
| 7,828,833 B2 | 11/2010 | Haverkost et al. | |
| 7,833,214 B2 | 11/2010 | Wilson et al. | |
| 7,846,139 B2 | 12/2010 | Zinn et al. | |
| 7,850,675 B2 | 12/2010 | Bell et al. | |
| 7,850,705 B2 | 12/2010 | Bachinski et al. | |
| 7,922,757 B2 | 4/2011 | McGuckin | |
| 7,972,314 B2 | 7/2011 | Bizup et al. | |
| 8,079,973 B2 | 12/2011 | Herrig et al. | |
| 8,092,435 B2 | 1/2012 | Beling et al. | |
| 8,097,311 B2 | 1/2012 | Wang et al. | |
| 8,313,524 B2 | 11/2012 | Edwin et al. | |
| 8,388,634 B2 | 3/2013 | Rubenstein et al. | |
| 8,512,312 B2 | 8/2013 | Sage | |
| 8,551,139 B2 | 10/2013 | Surti et al. | |
| 8,690,815 B2 | 4/2014 | Porter et al. | |
| 8,951,355 B2 | 2/2015 | Boyle, Jr. et al. | |
| 9,642,623 B2 | 5/2017 | Agarwal et al. | |
| 9,731,113 B2 | 8/2017 | Grace et al. | |
| 10,172,673 B2 | 1/2019 | Viswanathan et al. | |
| 2001/0053930 A1 | 12/2001 | Kugler et al. | |
| 2002/0049403 A1 | 4/2002 | Alanis | |
| 2002/0055766 A1 | 5/2002 | Wallace et al. | |
| 2002/0055771 A1 | 5/2002 | Sandock | |
| 2002/0069893 A1 | 6/2002 | Kawazoe | |
| 2002/0099432 A1 | 7/2002 | Yee | |
| 2002/0151761 A1 | 10/2002 | Viole et al. | |
| 2003/0100859 A1 | 5/2003 | Henderson et al. | |
| 2003/0131489 A1 | 7/2003 | Hsiao | |
| 2003/0135258 A1 | 7/2003 | Andreas et al. | |
| 2003/0135261 A1 | 7/2003 | Kugler et al. | |
| 2003/0139806 A1 | 7/2003 | Haverkost et al. | |
| 2003/0181969 A1 | 9/2003 | Kugler et al. | |
| 2003/0212385 A1 | 11/2003 | Brenner et al. | |
| 2003/0212431 A1 | 11/2003 | Brady et al. | |
| 2004/0024442 A1 | 2/2004 | Sowinkski et al. | |
| 2004/0054405 A1 | 3/2004 | Thierry et al. | |
| 2004/0073282 A1 | 4/2004 | Stanish | |
| 2004/0078071 A1 | 4/2004 | Escamilla et al. | |
| 2004/0092956 A1 | 5/2004 | Liddicoat et al. | |
| 2004/0099395 A1 | 5/2004 | Wang et al. | |
| 2004/0147866 A1 | 7/2004 | Blatter et al. | |
| 2004/0193242 A1 | 9/2004 | Lentz et al. | |
| 2004/0215058 A1 | 10/2004 | Zirps et al. | |
| 2004/0215337 A1 | 10/2004 | Hain et al. | |
| 2004/0236412 A1 | 11/2004 | Brar | |
| 2005/0004553 A1 | 1/2005 | Douk | |
| 2005/0137614 A1 * | 6/2005 | Porter | A61B 17/11 606/153 |
| 2005/0192559 A1 | 9/2005 | Michels et al. | |
| 2005/0203457 A1 | 9/2005 | Smego | |
| 2005/0209581 A1 | 9/2005 | Butts et al. | |
| 2005/0215938 A1 | 9/2005 | Khan et al. | |
| 2006/0004392 A1 | 1/2006 | Amarant | |
| 2006/0029465 A1 | 2/2006 | Auer | |
| 2006/0058867 A1 | 3/2006 | Thistle et al. | |
| 2006/0064159 A1 | 3/2006 | Porter et al. | |
| 2006/0081260 A1 | 4/2006 | Eells et al. | |
| 2006/0118236 A1 | 6/2006 | House et al. | |
| 2007/0038288 A1 | 2/2007 | Lye et al. | |
| 2007/0078412 A1 | 4/2007 | McGuckin, Jr. et al. | |
| 2007/0078416 A1 | 4/2007 | Eliasen | |
| 2007/0078438 A1 | 4/2007 | Okada | |
| 2007/0088336 A1 | 4/2007 | Dalton | |
| 2007/0123811 A1 | 5/2007 | Squitieri | |
| 2007/0135775 A1 | 6/2007 | Edoga et al. | |
| 2007/0142850 A1 | 6/2007 | Fowler | |
| 2007/0161958 A1 | 7/2007 | Glenn | |
| 2007/0167901 A1 | 7/2007 | Herrig et al. | |
| 2007/0168019 A1 | 7/2007 | Amplatz et al. | |
| 2007/0173868 A1 | 7/2007 | Bachinski et al. | |
| 2007/0179513 A1 | 8/2007 | Deutsch | |
| 2007/0191779 A1 | 8/2007 | Shubayev et al. | |
| 2007/0197856 A1 | 8/2007 | Gellman et al. | |
| 2007/0213838 A1 | 9/2007 | Hengelmolen | |
| 2007/0219510 A1 | 9/2007 | Zinn et al. | |
| 2007/0233018 A1 | 10/2007 | Bizup et al. | |
| 2007/0249986 A1 | 10/2007 | Smego | |
| 2007/0249987 A1 | 10/2007 | Gertner | |
| 2007/0265584 A1 | 11/2007 | Hickman et al. | |
| 2007/0293823 A1 | 12/2007 | Sherry | |
| 2007/0293829 A1 | 12/2007 | Conlon et al. | |
| 2008/0009781 A1 | 1/2008 | Anwar et al. | |
| 2008/0027534 A1 | 1/2008 | Edwin et al. | |
| 2008/0132924 A1 | 6/2008 | McGuckin | |
| 2008/0167595 A1 | 7/2008 | Porter et al. | |
| 2008/0221469 A1 | 9/2008 | Shevchuk | |
| 2008/0267688 A1 | 10/2008 | Busted | |
| 2008/0306580 A1 | 12/2008 | Jenson et al. | |
| 2009/0076587 A1 | 3/2009 | Cully et al. | |
| 2009/0137944 A1 | 5/2009 | Haarala et al. | |
| 2009/0179422 A1 | 7/2009 | Werth | |
| 2009/0227932 A1 | 9/2009 | Herrig | |
| 2009/0234267 A1 | 9/2009 | Ross | |
| 2009/0318895 A1 | 12/2009 | Lachner | |
| 2010/0154800 A1 | 6/2010 | Chang et al. | |
| 2010/0160847 A1 | 6/2010 | Braido et al. | |
| 2010/0161040 A1 | 6/2010 | Braido et al. | |
| 2010/0198079 A1 | 8/2010 | Ross | |
| 2010/0268188 A1 | 10/2010 | Hanson | |
| 2010/0268196 A1 | 10/2010 | Hastings et al. | |
| 2010/0292774 A1 | 11/2010 | Shalev | |
| 2011/0015723 A1 | 1/2011 | Batiste et al. | |
| 2011/0054312 A1 | 3/2011 | Bell et al. | |
| 2011/0060264 A1 | 3/2011 | Porter et al. | |
| 2011/0106019 A1 | 5/2011 | Bagwell et al. | |
| 2011/0112482 A1 | 5/2011 | Redd | |
| 2011/0196282 A1 | 8/2011 | Kassab | |
| 2011/0208218 A1 | 8/2011 | Ball | |
| 2011/0257609 A1 | 10/2011 | Bizup et al. | |
| 2011/0264080 A1 | 10/2011 | Lim et al. | |
| 2011/0295181 A1 | 12/2011 | Dann et al. | |
| 2012/0059305 A1 | 3/2012 | Akingba | |
| 2012/0065652 A1 | 3/2012 | Cully et al. | |
| 2012/0078202 A1 | 3/2012 | Beling et al. | |
| 2013/0060268 A1 | 3/2013 | Herrig | |
| 2013/0338559 A1 | 12/2013 | Franano et al. | |
| 2014/0018721 A1 | 1/2014 | Gage et al. | |
| 2014/0094841 A1 | 4/2014 | Sutton et al. | |
| 2014/0150782 A1 | 6/2014 | Vazales et al. | |
| 2014/0155908 A1 | 6/2014 | Rosenblath et al. | |
| 2014/0257244 A1 | 9/2014 | Johnston et al. | |
| 2014/0276215 A1 | 9/2014 | Nelson | |
| 2014/0288638 A1 | 9/2014 | Knight et al. | |
| 2014/0296822 A1 | 10/2014 | Chartrand | |
| 2014/0371779 A1 | 12/2014 | Vale et al. | |
| 2015/0051532 A1 | 2/2015 | Tomko et al. | |
| 2015/0082604 A1 | 3/2015 | Cully et al. | |
| 2015/0094744 A1 | 4/2015 | Aghayev et al. | |

(56) References Cited

U.S. PATENT DOCUMENTS

| | | |
|---|---|---|
| 2015/0150640 A1 | 6/2015 | Boyle et al. |
| 2015/0165496 A1 | 6/2015 | Moreau |
| 2015/0257775 A1 | 9/2015 | Gilvarry et al. |
| 2016/0066954 A1 | 3/2016 | Miller et al. |
| 2016/0120673 A1 | 5/2016 | Siegel et al. |
| 2016/0129177 A1 | 5/2016 | Herrig |
| 2016/0136398 A1 | 6/2016 | Heilman et al. |
| 2017/0020556 A1 | 1/2017 | Sutton et al. |
| 2017/0106128 A1 | 4/2017 | Bagwell et al. |
| 2019/0022368 A1 | 1/2019 | Hall et al. |

FOREIGN PATENT DOCUMENTS

| | | |
|---|---|---|
| DE | 102008055587 | 8/2009 |
| EP | 0540834 | 5/1993 |
| EP | 1797831 | 6/2007 |
| JP | 5714358 | 1/1982 |
| JP | 62112567 | 5/1987 |
| JP | 04507050 | 12/1992 |
| JP | 05212107 | 8/1993 |
| JP | 06105798 | 4/1994 |
| JP | 0984871 | 3/1997 |
| JP | 09264468 | 7/1997 |
| JP | 2003501223 | 1/2003 |
| JP | 3995057 | 10/2007 |
| JP | 2008511414 | 4/2008 |
| KR | 101026933 | 4/2011 |
| KR | 1020110036848 | 4/2011 |
| WO | 198403036 | 8/1984 |
| WO | 1990085509 | 8/1990 |
| WO | 199519200 | 7/1995 |
| WO | 199523553 | 9/1995 |
| WO | 199624399 | 8/1996 |
| WO | 1998034676 | 8/1998 |
| WO | 2000027299 | 5/2000 |
| WO | 200076577 | 12/2000 |
| WO | 200105447 | 1/2001 |
| WO | 200105463 | 1/2001 |
| WO | 2001005463 | 1/2001 |
| WO | 2001028456 | 4/2001 |
| WO | 200238198 | 5/2002 |
| WO | 2004032991 | 4/2004 |
| WO | 2004112880 | 12/2004 |
| WO | 2006026687 | 9/2006 |
| WO | 2007061787 | 5/2007 |
| WO | 2009059371 | 5/2009 |
| WO | 2009082513 | 7/2009 |
| WO | 2009120400 | 10/2009 |
| WO | 2010059102 | 5/2010 |
| WO | 2011060386 | 5/2011 |
| WO | 2011153302 | 12/2011 |
| WO | 2015023460 | 2/2015 |
| WO | 2015100251 | 7/2015 |
| WO | 2018164945 | 9/2018 |

OTHER PUBLICATIONS

International Search Report and Written Opinion dated Jan. 18, 2019 for PCT/US2018/041821.
Office Action dated Apr. 16, 2020 for U.S. Appl. No. 15/868,313.
Office Action dated Apr. 28, 2020 for U.S. Appl. No. 14/192,567.
Office Action dated Sep. 26, 2019 for U.S. Appl. No. 15/693,010.
Office Action dated May 1, 2020 for U.S. Appl. No. 15/693,010.
Office Action dated May 5, 2020 for U.S. Appl. No. 15/910,273.
European Search Report dated Jul. 24, 2020 for EP18738538.0.
European Search Report dated Jun. 8, 2005 for EP05006233.0.
European Search Report dated Dec. 3, 2013 for EP05793066.1.
International Preliminary Report dated Mar. 12, 2014 for PCT/US2012/053967.
International Search Report and Written Opinion dated Jan. 28, 2015 for PCT/US2014/049547.
International Search Report and Written Opinion dated Mar. 15, 2013 for PCT/US2012/053967.
International Search Report and Written Opinion dated Mar. 16, 2015 for PCT/US2014/046630.
International Search Report and Written Opinion dated May 2, 2018 for PCT/US2018/013326.
International Search Report and Written Opinion dated May 3, 2013 for PCT/US2012/053967.
International Search Report and Written Opinion dated May 6, 1998 for PCT/US1998/001939.
International Search Report and Written Opinion dated Jun. 3, 2009 for PCT/US2009/035923.
International Search Report and Written Opinion dated Jun. 20, 2007 for PCT/US2006/044564.
International Search Report and Written Opinion dated Jun. 22, 2018 for PCT/US2018/014371.
Notice of Allowance dated Mar. 15, 2010 for U.S. Appl. No. 11/216,536.
Notice of Allowance dated Oct. 4, 2013 for U.S. Appl. No. 12/831,092.
Office Action dated Jan. 9, 2018 for U.S. Appl. No. 14/450,468.
Office Action dated Feb. 6, 2013 for U.S. Appl. No. 12/831,092.
Office Action dated Feb. 21, 2017 for U.S. Appl. No. 14/192,567.
Office Action dated Mar. 15, 2018 for U.S. Appl. No. 14/332,091.
Office Action dated May 5, 2010 for U.S. Appl. No. 10/962,200.
Office Action dated May 24, 2018 for U.S. Appl. No. 14/995,270.
Office Action dated Jun. 4, 2018 for U.S. Appl. No. 14/192,567.
Office Action dated Jun. 9, 2016 for U.S. Appl. No. 14/192,567.
Office Action dated Jun. 15, 2017 for U.S. Appl. No. 14/192,567.
Office Action dated Jul. 11, 2018 for U.S. Appl. No. 14/450,468.
Office Action dated Aug. 7, 2017 for U.S. Appl. No. 14/450,468.
Office Action dated Aug. 12, 2010 for U.S. Appl. No. 10/962,200.
Office Action dated Aug. 15, 2016 for U.S. Appl. No. 14/332,091.
Office Action dated Sep. 20, 2012 for U.S. Appl. No. 12/831,092.
Office Action dated Oct. 27, 2015 for U.S. Appl. No. 14/192,567.
Office Action dated Nov. 26, 2007 for U.S. Appl. No. 10/962,200.
Office Action dated Dec. 5, 2017 for U.S. Appl. No. 14/995,270.
Office Action dated Dec. 20, 2017 for U.S. Appl. No. 14/192,567.
Office Action dated Dec. 30, 2016 for U.S. Appl. No. 14/450,468.
Clinical Reveiw of MTI, Onxy Liquid Embolization System, available at http://www.fda.gov/ohrms/dockets/ac/03/briefing/3975b1-02-clinical-review pdf. accessed Aug. 29, 2005.
Besarab, et al.,Measuring the Adequacy of Hemodialysis Access, Current Opinion in Nephrology and Hypertension, Rapid Science Publishers ISSN ,1996 ,1062-4821.
Coulson MD, et al.,Modification of Venous End of Dialysis Grafts: An Attempt to Reduce Neointimal Hyperplasia, Dialysis & Transplantation, vol. 29 No. 1 ,Jan. 2000 ,10-18.
Coulson MD, PhD, et al.,A Combination of the Elephant Trunk Anastomosis Technique and Vascular Clips for Dialysis Grafts, Surgical Rounds ,Nov. 1999 ,596-608.
Kanterman, et al.,Dialysis Access Grafts: Anatomic Location of Venous Stenosis and Results of Angioplasty, Interventional Radiology, vol. 195 No. 1, 195 ,Apr. 1995 ,135-139.
Kumpe, et al.,Angioplasty/Thrombolytic Treatment of Failing and Failed Hemodialysis Access Sites: Comparison with Surgical Treatment, Progress in Cardiovascular Diseases, vol. XXXIV No. 4 ,Jan./Feb. 1992 ,263-278.
Lin, et al.,Contemporary Vascular Access Surgery for Chronic Haemodialysis, They Royal College of Surgeons of Edinburgh, J.R. Coll, Surg, Edinb., 41 ,Jun. 1996 ,164-169.
Peterson, et al.,Subclavian Venous Stenosis: A Complication of Subclavian Dialysis, The Journal of American Medical Association, vol. 252 No. 24 ,Dec. 28, 1994 ,3404-3406.
Raju M.D., et al.,Techniques for Insertion and Management of Complications, PTFE Grafts for Hemodialysis Access, Ann. Surg., vol. 206 No. 5 ,Nov. 1987 ,666-673.
Sharafuddin, et al.,Percutaneous Balloon-Assisted Aspiration Thrombectomy of clotted ahemodialysis Access Grafts, Journal of Vascular and Interventional Radiology, vol. 7 No 2 ,Mar.-Apr. 1996 ,177-183.
International Search Report and Written Opinion dated Jun. 15, 2018 for PCT/US2018/020614.
International Search Report and Written Opinion dated Jul. 17, 2018 for PCT/US2018/023956.

(56) References Cited

OTHER PUBLICATIONS

International Search Report and Written Opinion dated Oct. 30, 2018 for PCT/US2018/042900.
Notice of Allowance dated Oct. 5, 2018 for U.S. Appl. No. 15/093,622.
Notice of Allowance dated Nov. 6, 2018 for U.S. Appl. No. 14/995,270.
Office Action dated Jan. 8, 2019 for U.S. Appl. No. 15/035,626.
Office Action dated Jul. 19, 2018 for U.S. Appl. No. 15/035,626.
Office Action dated Oct. 1, 2018 for U.S. Appl. No. 14/332,091.
Office Action dated Dec. 5, 2018 for U.S. Appl. No. 14/450,468.
Office Action dated Dec. 7, 2018 for U.S. Appl. No. 14/192,567.
European Search Report dated Oct. 26, 2020 for EP18738538.0.
Office Action dated Oct. 1, 2020 for U.S. Appl. No. 15/868,313.
European Search Report dated Dec. 4, 2020 for 18764826.6.
Office Action dated Nov. 30, 2020 for U.S. Appl. No. 15/910,273.
European Search Report dated Mar. 22, 2021 for EP18832124.4.
Notice of Allowance dated Mar. 24, 2021 for U.S. Appl. No. 15/910,273.

* cited by examiner

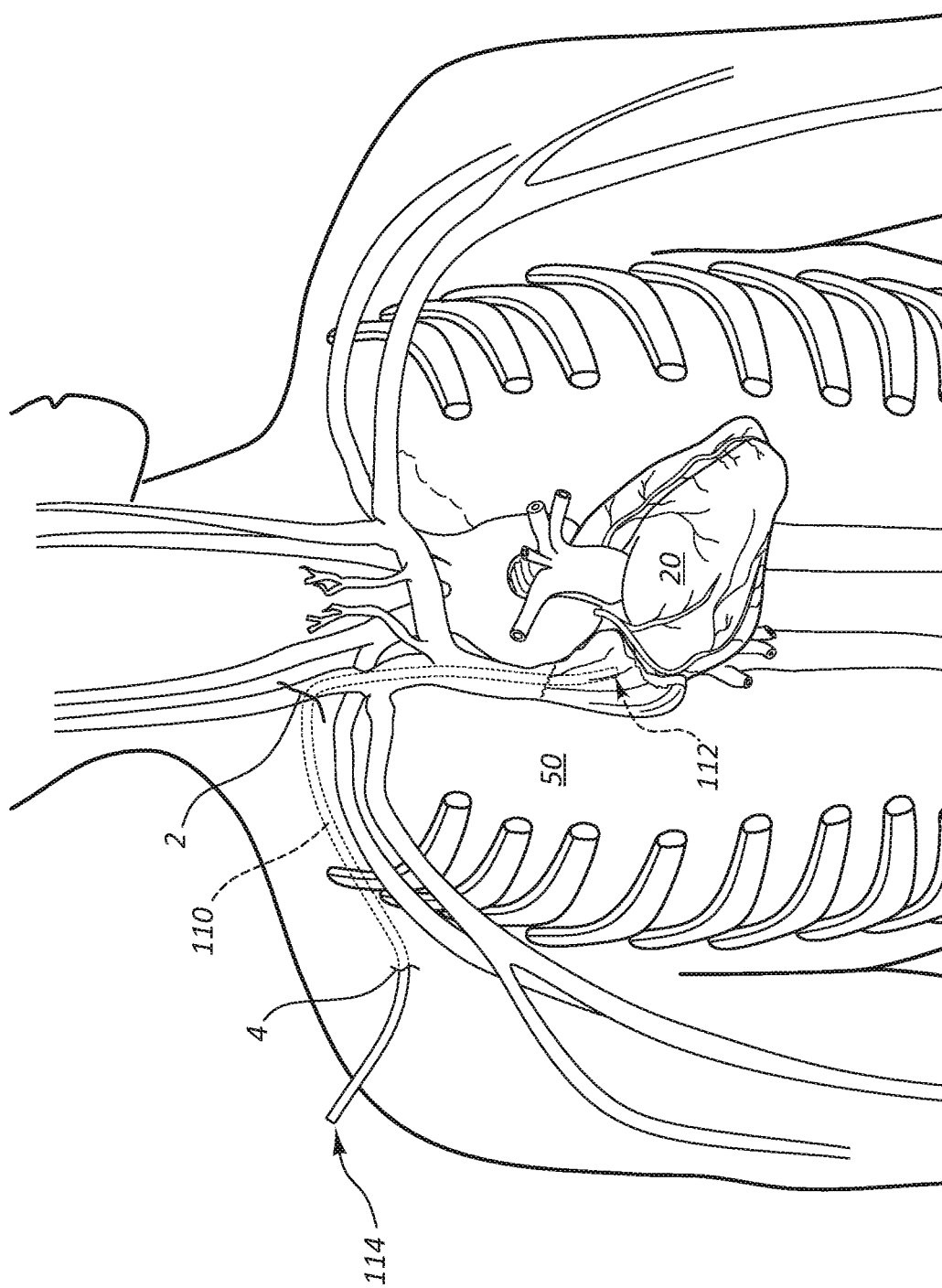

RELEASABLE CONDUIT CONNECTORS

RELATED APPLICATIONS

This application claims priority to U.S. Provisional Application No. 62/532,577, filed on Jul. 14, 2017 and titled "Releasable Conduit Connectors" which is hereby incorporated by reference in its entirety.

TECHNICAL FIELD

The present disclosure relates generally to the field of medical devices. More particularly, some embodiments relate to medical assemblies and devices for improving blood flow to regions of a patient's body.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 2B depicts the first tubular conduit placed into the patient such that a peripheral end of the first tubular conduit is disposed adjacent an incision in the shoulder region of the patient.

DETAILED DESCRIPTION

Figure 1:
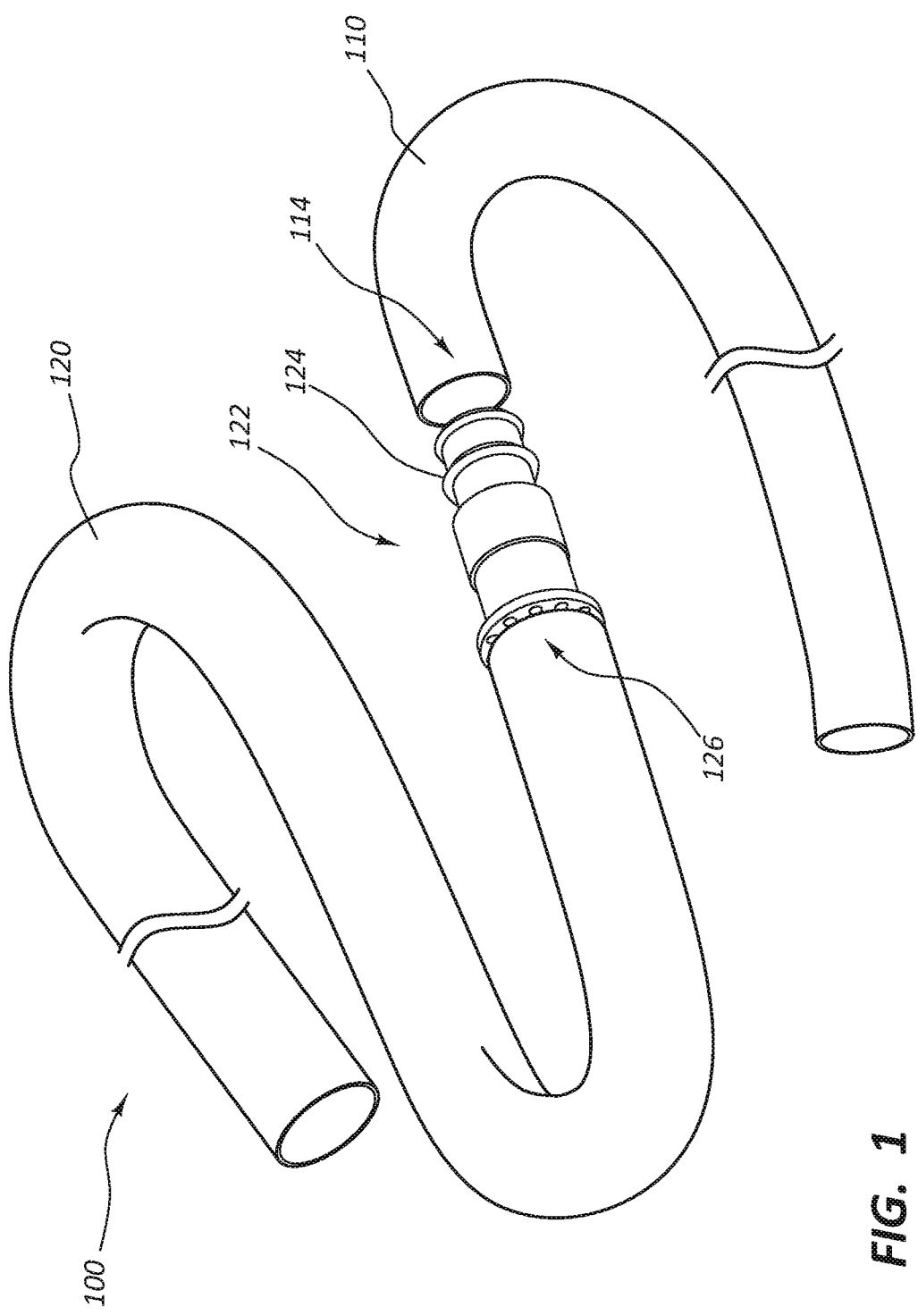
FIG. 1 is a perspective view of an embodiment of a vascular access assembly.

Many patients who suffer from kidney malfunction undergo hemodialysis to remove waste products from their blood. Hemodialysis generally requires access to an adequate blood supply. In some cases, access to a blood supply may be established via an arteriovenous fistula. In other circumstances, other methods for accessing the blood supply are used.

For example, in some embodiments, access to a blood supply is established via an arteriovenous graft. In other embodiments, access to a blood supply is established via a graft that extends from a peripheral blood supply to an outlet that is positioned in the central venous system.

Certain embodiments disclosed herein may be used to establish an artificial blood flow path, such as along a non-natural or artificial conduit, that improves or provides alternative access to a blood supply. The artificial flow path may be used, for example, to bypass a central venous stenosis. In some embodiments, the artificial blood flow path, when implanted into a patient, is fully subcutaneous. Access to a blood supply that is provided by an artificial flow path may be particularly advantageous for access in hemodialysis patients (such as hemodialysis patients who have exhausted peripheral venous access sites for fistulas).

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities. Thus, two components may be coupled to each other even though they are not in direct contact with each other. For example, two components may be coupled to each other through an intermediate component. The phrase "attached to" refers to interaction between two or more entities which are in direct contact with each other and/or are separated from each other only by a fastener of any suitable variety (e.g., an adhesive). The phrase "fluid communication" is broad enough to refer to arrangements in which a fluid (e.g., blood) can flow from one element to another element when the elements are in fluid communication with each other. Unless otherwise stated, all ranges include both endpoints and all numbers between the endpoints.

The terms "central" and "peripheral," as used herein, are opposite directional terms along a flow path of the vasculature. For example, a peripheral end of a device or component is the end of the device or component that is furthest from the heart when the device or component is assembled and implanted within the patient. The central end portion refers to the opposite end or the end closest to the heart of the patient when the device is in use. Further, this reference frame is applied herein to devices configured or designed to have one end (a central end) positioned closer to the heart when the device is in use, whether or not the device itself is deployed within the body.

FIG. 1 provides a perspective view of a vascular access assembly 100. As shown, the vascular access assembly 100 can include a first tubular conduit 110, a second tubular conduit 120, and one or more connectors or adaptors 122. In some embodiments, the first tubular conduit 110 may have an initial length of at least 20 cm, at least 25 cm, at least 30 cm, or at least 35 cm. For example, the first tubular conduit 110 may have an initial length of between about 20 cm and about 50 cm or between about 35 cm and about 45 cm. In certain embodiments, the first tubular conduit 110 has an internal diameter of between about 3.5 mm and about 6.5 mm. For example, the internal diameter of the first tubular conduit 110 may be between about 4.5 mm and about 5.5 mm.

In various embodiments, the first tubular conduit 110 may be resistant to kinking and/or crush forces. The first tubular conduit 110 may be reinforced. For example, the first tubular conduit 110 may be reinforced with nitinol, such as braided nitinol, which can provide resistance to kinking and/or crush forces. More specifically, in various embodiments, the first tubular conduit 110 may include silicone-coated nitinol.

In some embodiments, the first tubular conduit 110 may include one or more radiopaque bands or markers (not shown). For example, the first tubular conduit 110 may include a radiopaque band adjacent the central end portion of the first tubular conduit 110. The radiopaque band(s) or marker(s) may facilitate fluoroscopic placement of the first tubular conduit 110 within a patient.

In certain embodiments, the second tubular conduit 120 may be configured to be accessed for hemodialysis. In other words, during some medical procedures (e.g., hemodialysis), the second tubular conduit 120 may be accessed in lieu of the natural vasculature of a patient. In various embodiments, the second tubular conduit 120 may include and/or consist of polytetrafluoroethylene (PTFE) (e.g., such as expanded PTFE (ePTFE), rotational spun PTFE, or electrospun PTFE). In various other embodiments, the second tubular conduit 120 may include silicone, a fibrous polymer, or another suitable material.

In some embodiments, the second tubular conduit 120 may include a puncturable and self-sealing wall such that the wall may be punctured by insertion of a needle and then reseal upon withdrawal of the needle. The self-sealing wall may be of any suitable composition. In certain embodiments, the self-sealing wall may be a multi-layered construct. For example, the self-sealing wall may include an outer layer, an inner layer, and at least one tie layer disposed between the outer layer and the inner layer. One or more of the outer layer and the inner layer may include PTFE. For example, the outer layer may include and/or consist of expanded PTFE while the inner layer may include and/or consist of rotational spun or electrospun PTFE. The tie layer may include an elastomer such as elastomeric silicone. Due, at least in part, to the properties of the silicone, the resulting construct may be self-sealing. In other words, when a needle that has been inserted through the wall is withdrawn from the second tubular conduit 120, the wall may seal itself, thereby preventing leakage of blood from the second tubular conduit 120.

In various embodiments, the second tubular conduit 120 may have an initial length of at least 30 cm, at least 40 cm, or at least 45 cm. For example, the second tubular conduit 120 may be between about 30 cm and about 70 cm or between about 40 cm and about 60 cm in length. In some embodiments, the second tubular conduit 120 may have an internal diameter of between about 4.5 mm and about 8 mm. For example, the internal diameter of the second tubular conduit 120 may be between about 5.5 mm and about 6.5 mm.

In some embodiments, both the first tubular conduit 110 and the second tubular conduit 120 may be self-sealing. In some other embodiments, only the second tubular conduit 120 may be self-sealing.

In certain embodiments, one or both of an inner surface and an outer surface of the vascular access assembly 100 may be associated with a therapeutic agent. In other words, the therapeutic agent may be disposed on or embedded within a surface of the vascular access assembly 100. The therapeutic agent may be released from the surface(s) of the vascular access assembly 100 to deliver a therapeutically effective dose of the therapeutic agent to the patient when the vascular access assembly 100 is implanted within a patient. In various embodiments, a first therapeutic agent is associated with the inner surface of the vascular access assembly 100 and a second therapeutic agent that differs from the first therapeutic agent is associated with the outer surface of the vascular access assembly 100. In such embodiments, both the first therapeutic agent and the second therapeutic agent may be delivered into the bloodstream of the patient in therapeutically effective doses when the vascular access assembly 100 is implanted within the patient. In some embodiments, heparin may be used as a therapeutic agent. The therapeutic agent may reduce or be configured to reduce thrombus or tissue proliferation.

With continued reference to FIG. 1, the one or more connectors 122 may facilitate coupling of the first tubular conduit 110 to the second tubular conduit 120, or vice versa. In certain embodiments, such as the embodiment shown in FIG. 1, the connector 122 can be disposed at a central end 126 the second tubular conduit 120.

As depicted, the connector 122 may include one or more barbs or protrusions 124 that are designed to engage with an inner surface of the first tubular conduit 110 to form a fluid-tight connection. In some embodiments, any attempt to remove the first tubular conduit 110 from the connector 122 may cause the first tubular conduit 110 to "neck down" or become narrower in diameter, thereby causing the first tubular conduit 110 to more tightly engage with the connector 122. While FIG. 1 shows the connector 122 at the central end 126 of the second tubular conduit 120, a skilled artisan, having the benefit of this disclosure, will recognize that, in other embodiments, the connector 122 may instead be disposed at a peripheral end 114 of the first tubular conduit 110. In still other embodiments, the connector 122 may include components disposed at both the central end 126 of the second tubular conduit 120 and the peripheral end 114 of the first tubular conduit 110. The connector 122 may be made from any suitable material, such as a metal (e.g., steel or titanium), a polymer, etc.

The vascular access assembly 100 may be used in any suitable medical procedure, such as to establish vascular access for hemodialysis. For example, where a vein has become stenotic or otherwise failed an artificial flow path that bypasses the stenosis or failure may be established. Stated another way, an artificial flow path may be established from a target site (e.g., from a target site in a vessel, artery, arteriovenous graft, etc.) to the vena cava or right atrium of the heart. Various examples herein discuss access and therapies performed in the right atrium of the heart. These examples and related disclosure may be analogously applied to access and therapies performed at adjacent locations such as the vena cava or the venous vasculature around the vena cava. Still further, the assemblies discussed herein may be utilized to create synthetic blood flow paths in other areas of the body as well and disclosure relative to specific examples, such as placement of a device in the right atrium, may be analogously applied to other areas of the body.

Figure 2A:
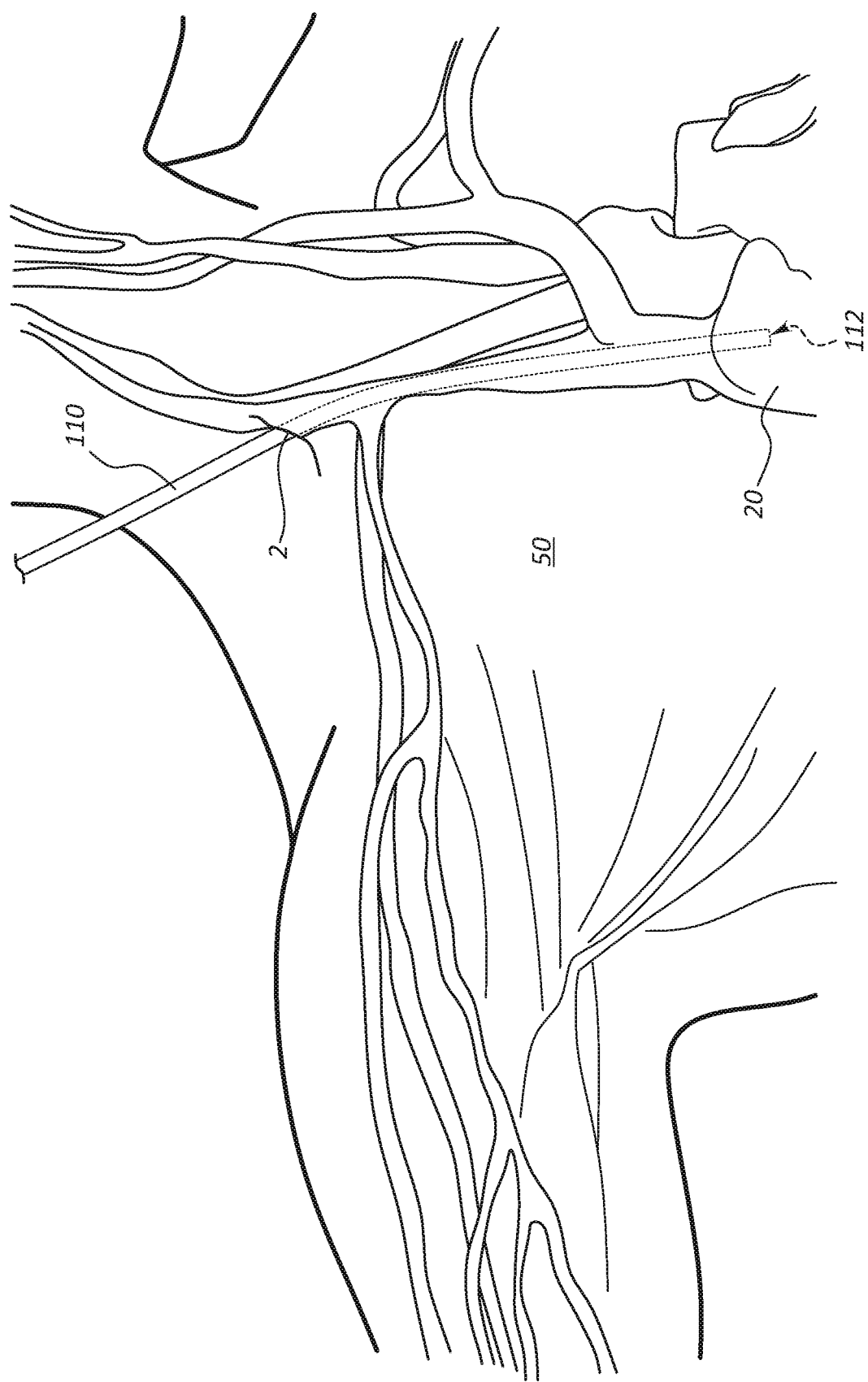
FIG. 2A depicts a first tubular conduit of the vascular access assembly of FIG. 1 that has been inserted into a patient such that a central end portion of the first tubular conduit is disposed within the right atrium of the patient.

As shown in FIG. 2A, a medical procedure for placement within the right atrium may initially involve making a first incision 2 at or adjacent to the neck of a patient 50 to access the right internal jugular vein of the patient 50. A guidewire may then be passed into the right internal jugular vein to the inferior vena cava, followed by a dilator that is passed over the guidewire to facilitate insertion of an introducer. The dilator may then be removed, and the introducer passed over the guidewire into the right internal jugular vein of the patient 50. Once the introducer is placed within the right internal jugular vein, a central end portion 112 of the first tubular conduit 110 may be inserted through the introducer and advanced within the patient 50 such that the central end portion 112 of the first tubular conduit 110 passes through the superior vena cava into the right atrium of a heart 20 (e.g., the mid to upper right atrium) as depicted in FIG. 2A. Advancement of the first tubular conduit 110 into the patient 50 may be done under fluoroscopic guidance. Notwithstanding specific examples wherein the first tubular conduit 110 is partially disposed within a body lumen or bodily structure, it is within the scope of this disclosure for the first tubular conduit 110 to be attached to a vessel or other structure, though not disposed within that vessel or structure, for example the first tubular conduit 110 may be coupled to a vessel by a sutured anastomosis. Thus, in some instances, systems within the scope of this disclosure may comprise multiple conduits coupled to each other by connectors wherein one or all the conduits are also coupled to a vessel without being disposed within the vessel.

After the central end portion 112 of the first tubular conduit 110 has been placed within the right atrium of the heart 20, a second incision 4 (see FIG. 2B) may be made in the shoulder region of the patient 50 (e.g., adjacent the deltopectoral groove). A tunneling device may then be used to establish a subcutaneous path between the first incision 2 in the neck region of the patient 50 and the second incision 4 in the shoulder region of the patient 50. The peripheral end 114 of the first tubular conduit 110 may then be inserted into the first incision 2 and advanced along the path established by the tunneling device (i.e., the first tubular conduit 110 is tunneled) such that the first tubular conduit 110 extends from the right atrium of the heart 20 to the second incision 4 in the shoulder region of the patient 50 as shown in FIG. 2B.

Figure 2C:
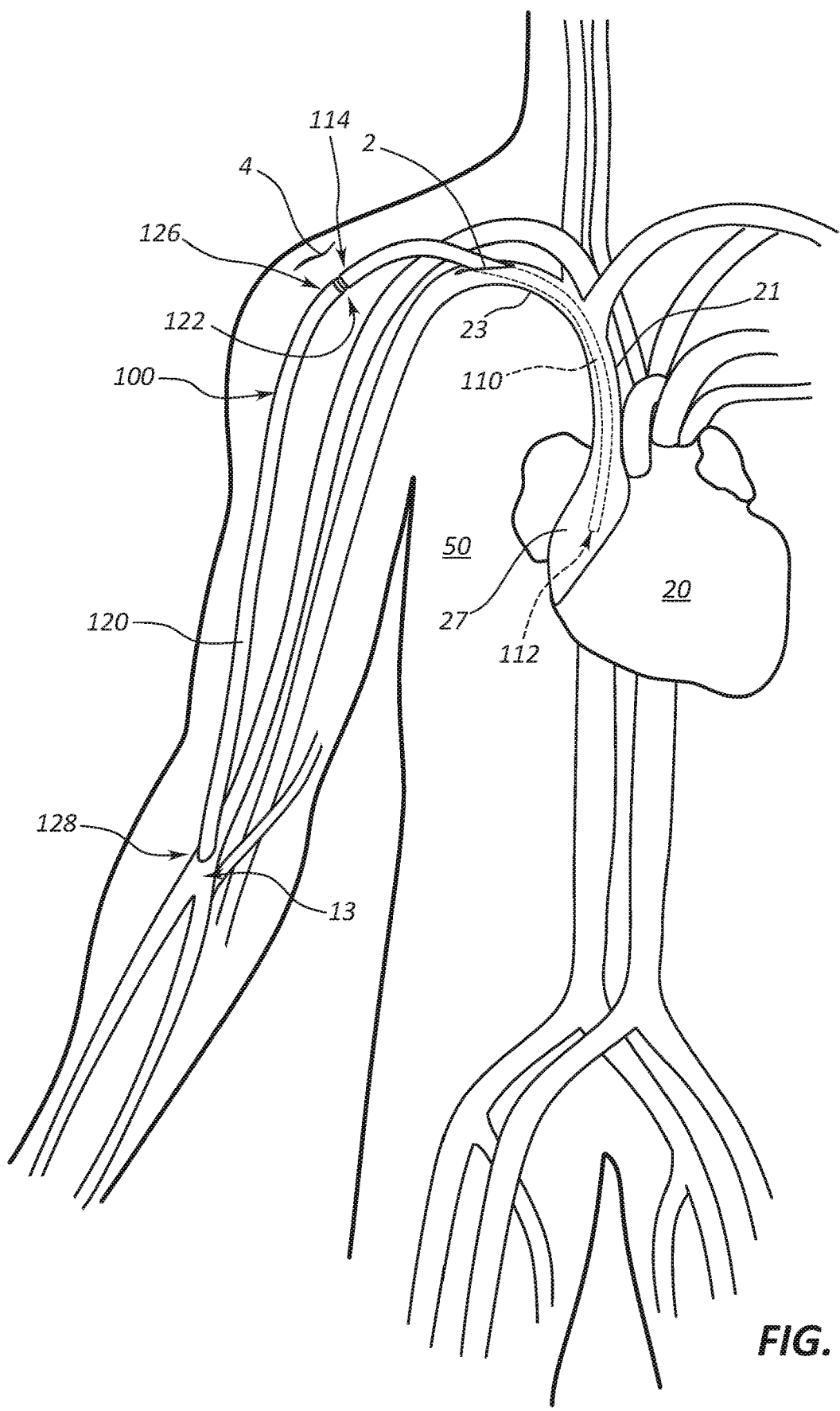
FIG. 2C depicts a second tubular conduit of the vascular access assembly of FIG. 1 that has been inserted into the patient such that the second tubular conduit extends from the incision in the shoulder region of the patient to a target site.

Once the first tubular conduit 110 has been placed such that the first tubular conduit 110 extends from the right atrium of the heart 20 to the second incision 4 in the shoulder region of the patient 50, an incision may be made at a target site 13, for example, in an artery as depicted. In some other embodiments, the target site 13 may be in an arteriovenous graft, a vein, or another suitable position. A tunneling device may then be used to establish a subcutaneous path between the second incision 4 in the shoulder region of the patient 50 to the target site 13, A peripheral end 128 of the second tubular conduit 120 may then be inserted into the second incision 4 and advanced along the path established by the tunneling device (i.e., the second tubular conduit 120 is tunneled) such that the second tubular conduit 120 extends from the second incision 4 in the shoulder region of the patient 50 to the target site 13 as shown in FIG. 2C.

With the central end portion 112 of the first tubular conduit 110 disposed within the right atrium of the heart 20 of the patient 50, the peripheral end 114 of the first tubular conduit 110 may then, if needed, be cut to the appropriate length. In other words, the first tubular conduit 110 may initially (e.g., when manufactured and inserted as described above) have a length that is longer than is needed to establish a flow path from the right atrium of the heart 20 of the patient 50 to the second incision 4 in the shoulder region of the patient 50. The first tubular conduit 110 may then be cut to proper length to facilitate coupling of the second tubular conduit 120 to the first tubular conduit 110 at the second incision 4 in the shoulder region of the patient 50. As depicted, the central end 126 of the second tubular conduit 120 may be coupled to the peripheral end 114 of the first tubular conduit 110 via the connector 122.

Similarly, in some embodiments, the second tubular conduit 120 may have an initial length that is longer than is needed to establish a flow path from the second incision 4 in the shoulder region of the patient 50 to the target site 13. In such embodiments, the central end 126 of the second tubular conduit 120 may be cut to the appropriate length once the second tubular conduit 120 has been inserted into the patient 50. In some embodiments, the connector 122 may then be attached to the newly formed central end portion of the second tubular conduit 120. In some other embodiments, no cutting of the second tubular conduit 120 may be needed.

Once the first tubular conduit 110 and the second tubular conduit 120 are the proper length, the second tubular conduit 120 may be coupled to the first tubular conduit 110, or vice versa. For example, the connector 122 at the central end 126 of the second tubular conduit 120 may be inserted into the peripheral end 114 of the first tubular conduit 110 such that the barbs or protrusions 124 of the connector 122 engage with an inner surface of the first tubular conduit 110 (see FIG. 1). Such engagement may establish a fluid-tight connection between the first tubular conduit 110 and the second tubular conduit 120. Establishment of a fluid-tight connection can be confirmed by attaching the peripheral end 128 of the second tubular conduit 120 to a syringe and advancing fluid (e.g., heparinized saline) through the system.

The peripheral end 128 of the second tubular conduit 120 may be coupled to an artery at the target site 13. For example, an incision may be made at the target site 13 and an arterial anastomosis may be performed between the peripheral end 128 of the second tubular conduit 120 and the target site 13. Coupling of a portion of the vascular access assembly 100 (e.g., the peripheral end 128 of the second tubular conduit 120) to an artery may be performed via any suitable technique. Once a flow path from the target site 13 to the heart 20 has been established as shown in FIG. 2C, the first incision 2 and the second incision 4 may be closed via any suitable technique. In this manner, the vascular access assembly 100 may, when implanted and assembled, be a fully subcutaneous surgical implant. Furthermore, the implanted and assembled vascular access assembly 100 may, as described above, be implanted without establishing a venous anastomosis.

The implanted vascular access assembly 100 may be used to facilitate vascular access. For example, in the case of hemodialysis, a practitioner may insert a first needle through the skin of the patient 50 and into the vascular access assembly 100. More particularly, the first needle may be inserted into the second tubular conduit 120. Fluid may be withdrawn from the vascular access assembly 100 and drawn into a dialysis machine that purifies the blood. The purified blood may then be returned to the patient 50 via a second needle that extends through the skin of the patient 50 and into a more central location of the second tubular conduit 120.

The steps of the procedure described above are only exemplary in nature. In other words, the vascular access assembly 100 may be implanted into the patient 50 via a procedure that deviates somewhat from the procedure described above. One of ordinary skill in the art, having the benefit of this disclosure, will also appreciate that some of the steps described above need not be performed in the order that is specified above.

An additional aspect of the disclosure relates to methods of accessing an implanted vascular access assembly 100. A practitioner may desire to access the vascular access assembly 100 so that the practitioner may clean or clear at least a portion of the vascular access assembly 100. In some embodiments, the vascular access assembly 100, or at least a portion of the vascular access assembly 100, may become occluded and/or blocked during use. For example, a blood clot or other embolus may develop within at least a portion of the vascular access assembly 100. Accordingly, the practitioner may access the vascular access assembly 100 to remove the blood clot or other embolus from within the vascular access assembly 100. In an effort to streamline the disclosure, the methods provided herein generally refer to the removal of a blood clot from the vascular access assembly 100. The provided methods, however, may also be used and/or adapted for the removal of other types of emboli from within the vascular access assembly 100 (e.g., fatty deposits, tissue growths, etc.).

In some embodiments, methods of declotting the vascular access assembly 100 may further include decoupling the first tubular conduit 110 and the second tubular conduit 120, for example, at the connector 122. The practitioner may then couple a flushing mechanism (not shown) to the peripheral end 114 of the first tubular conduit 110. The flushing mechanism may be a component of the vascular access assembly declotting system. In certain embodiments, the flushing mechanism may include a flushing catheter, wherein a peripheral end portion of the flushing catheter is in fluid communication with a fluid source (e.g., a source of a saline solution or another suitable fluid). Upon coupling of the flushing mechanism and the first tubular conduit 110, the practitioner may displace a fluid through at least a portion of the flushing mechanism and through at least a portion of the first tubular conduit 110.

In some embodiments, a practitioner may couple a vacuum source to a peripheral end 114 of the first tubular conduit 110. In certain embodiments, the vacuum source may be coupled to the first tubular conduit 110 via a vacuum catheter. In some embodiments, the vacuum source and/or the vacuum catheter may be components of the vascular access assembly declotting system.

The vacuum source may be activated (e.g., by the practitioner) such that a suction force is applied on the first tubular conduit 110 and a clot disposed within the first tubular conduit 110 can be displaced from within, evacuated from, or sucked out of the first tubular conduit 110.

In some embodiments, the first tubular conduit 110 and the second tubular conduit 120 may be decoupled and a low-profile balloon may be fed via a guidewire through either the first tubular conduit 110 or the second tubular conduit 120. The low-profile balloon may be slid through the clot and then inflated and pulled out the respective tubular conduit 110 or 120 via the guidewire to remove the clot.

Preferably, in each of the declotting methods, the first tubular conduit 110 and the second tubular conduit 120 can be decoupled without damage and recoupled once the clot is removed.

Therefore, in some embodiments, the vascular access system includes a releasable connector such that the first tubular conduit 110 and the second tubular conduit 120 may be decoupled to make adjustments to either the first tubular conduit 110 or the second tubular conduit 120 during implantation, after implantation, or to declot, as discussed above, one or the other of the first tubular conduit 110 and the second tubular conduit 120. After adjustments or declotting, the first tubular conduit 110 and the second tubular conduit 120 may be recoupled together without removing or damaging either the first tubular conduit 110 or the second tubular conduit 120.

Figure 3:
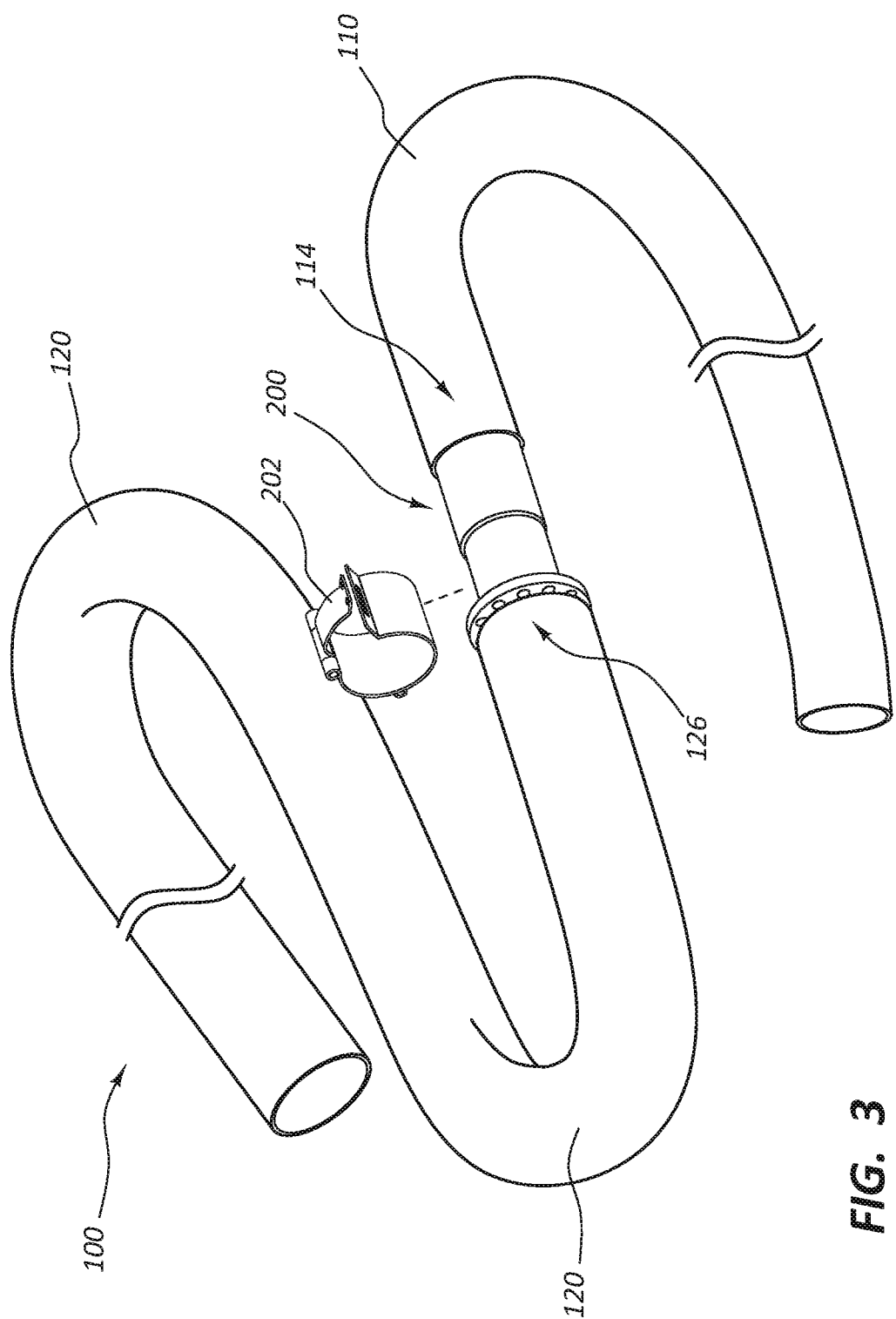
FIG. 3 is a perspective view of an embodiment of a vascular access assembly.
Figure 4:
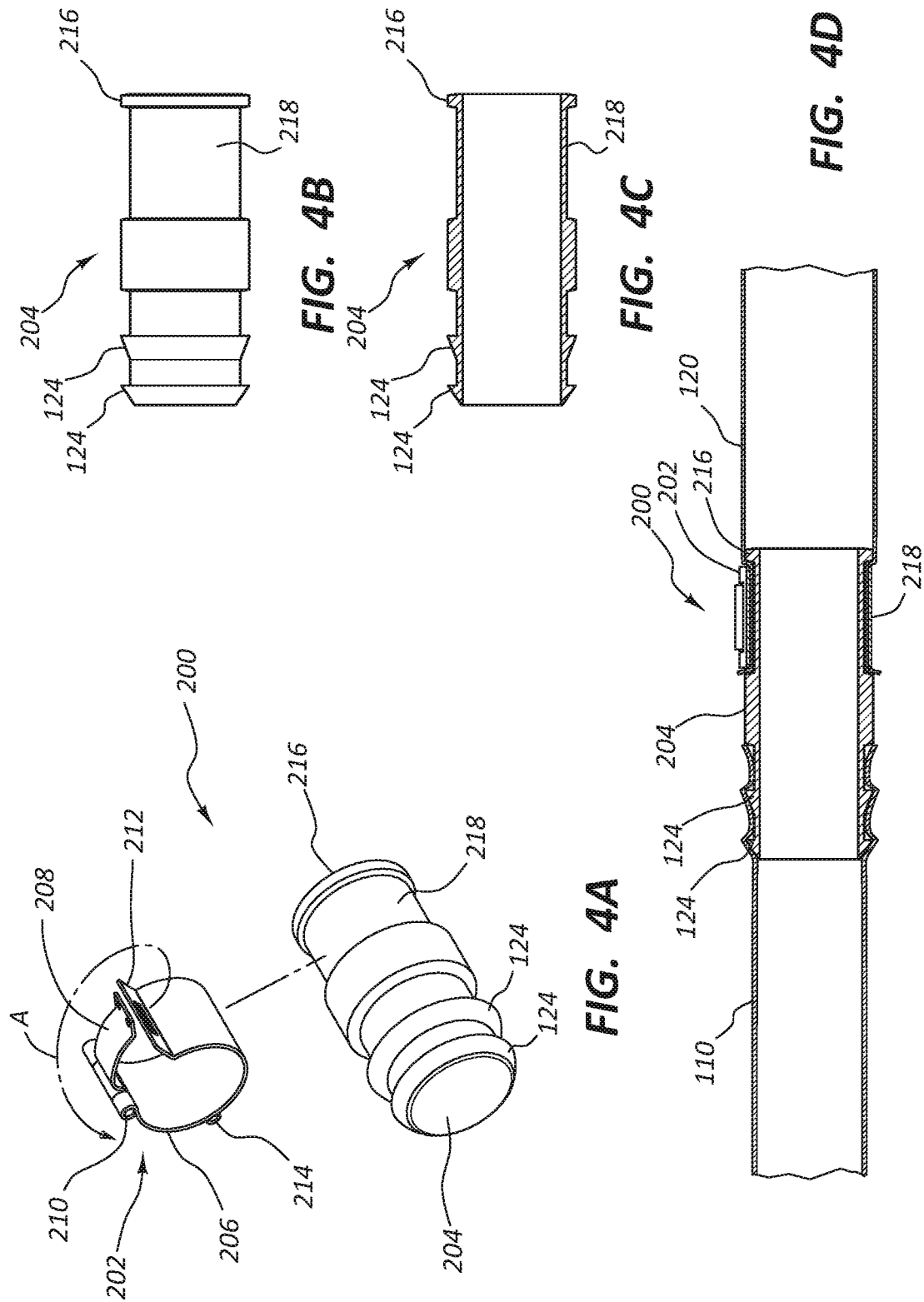
FIG. 4A depicts a perspective view of the connector assembly of FIG. 3.
FIG. 4B depicts a side view of the connector body of FIG. 3.
FIG. 4C depicts a cross-section view of the connector body of FIGS. 4B and 3.
FIG. 4D depicts a cross-section view of the connector assembly of FIG. 3 engaged with tubular conduits of the vascular access system.

FIG. 3 depicts an alternative embodiment of a releasable connector assembly 200. FIGS. 4A-4D show various views of a connector assembly 200 having a releasable connection portion 202 and a connector body 204. The releasable connection portion 202 may include a C-shaped body portion 206 that forms a split ring. A handle 208 is connected to one end of the C-shaped body portion 206. The handle 208 is hinged via a pin 210 and moves in the direction of arrow A to place the releasable connection portion 200 in a locked position. In some embodiments, the handle 208 may engage with a slot 212 to lock the releasable connection portion 202. When in a locked position, a suture may be knotted to a post 214 to prevent handle 208 from moving to an unlocked position. The releasable connection portion 202 may be used to prevent either the first tubular conduit 110 or the second tubular conduit 120 from decoupling during the lock position, but provide decoupling when in the unlocked position.

For example, as seen in FIG. 4B, which shows a side view of the connector body 204, and as seen in FIG. 4C, which shows a cross-sectional view of the connector body 204, barbs 124 may be included on the connector body 204. Any attempt to remove the first tubular conduit 110 from the connector body 204 may cause the first tubular conduit 110 to "neck down" or become narrower in diameter, thereby causing the first tubular conduit 110 to more tightly engage with connector body 204. The connector body 204 may also include a protrusion 216. As shown in FIG. 4D, the second tubular conduit 120 may be disposed over the protrusion 216, but may be removed from the connector body 204 over the protrusion 216 without any damage to the second tubular conduit 120. The releasable connection portion 202 locks into position over the second tubular conduit 120 in a releasable connector area 218. The releasable connection portion 202 and connector assembly 200 provide a fluid-tight connection between the first tubular conduit 110 and the second tubular conduit 120.

While FIG. 3 and FIGS. 4A-4D show the connector assembly 200 irremovably connected at the first tubular conduit 110 and removably connected at the second tubular conduit 120, a skilled artisan, having the benefit of this disclosure, will recognize that, in other embodiments, the connector assembly 200 may instead be irremovably connected to the second tubular conduit 120 and removably connected at the first tubular conduit 110. In other embodiments, the first tubular conduit 110 and the second tubular conduit 120 may both be removably connected to the connector assembly 200. For example, rather than barbs 124, the connector body 204 may include two protrusions 216 and two releasable connection portions 202 may be provided.

Figure 5:
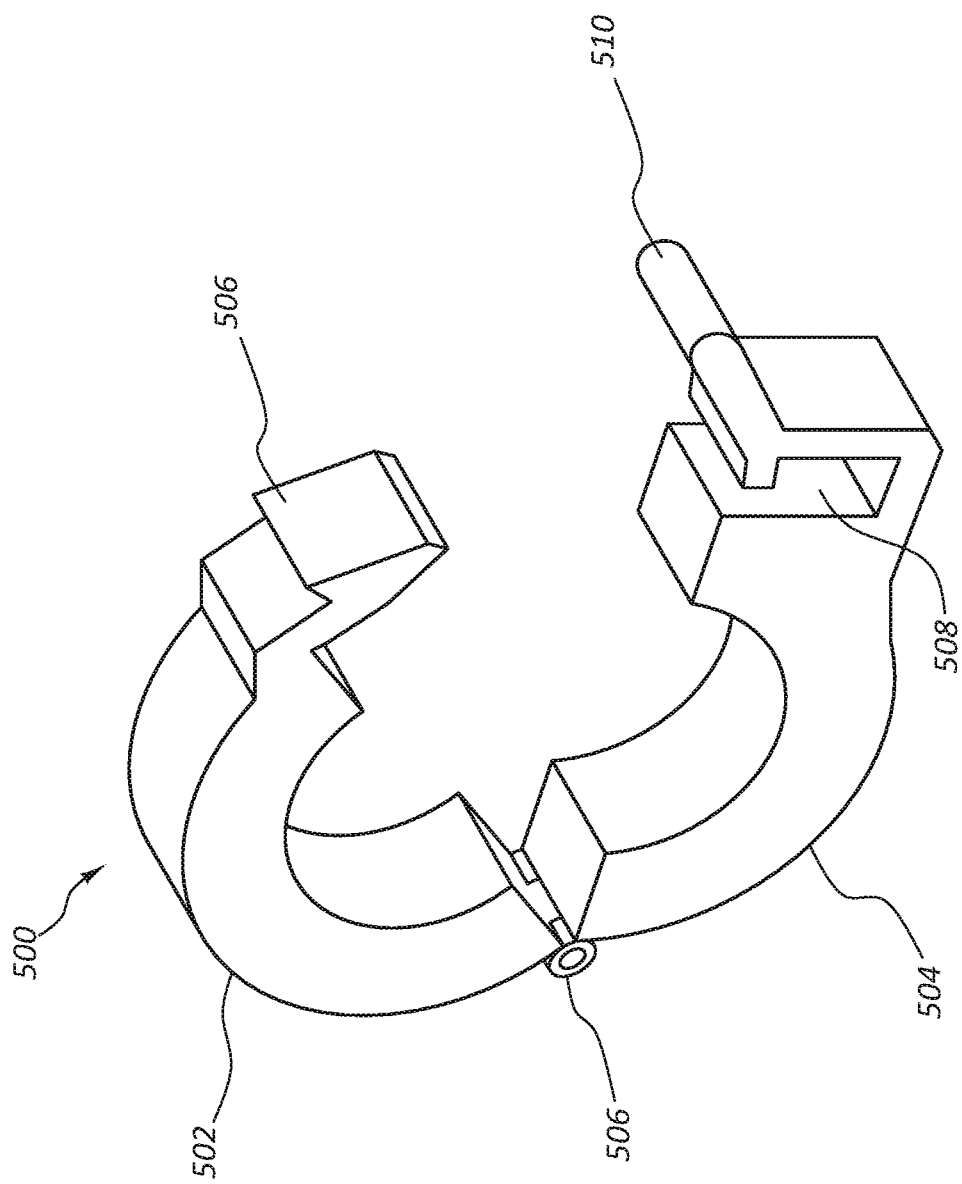
FIG. 5 depicts another embodiment of a releasable connection portion of FIG. 3.

The releasable connection portion 202 may be any type of releasable connector that creates a fluid-tight connection between the first tubular conduit 110 and the second tubular conduit 120. FIG. 5 depicts an alternative embodiment of a releasable connection portion 500 that may be used in place of the releasable connection portion 202. In this embodiment, a ring-structure is provided with two halves 502, 504 connected via a hinge 506. The releasable connection portion 500 is depicted in an unlocked position in FIG. 5. The releasable connection portion 500 may be disposed in a locked position in the releasable connector area 218. Half 502 of the ring-structure may include a protrusion 506. Protrusion 506 includes a lip that engages with a slot 508 of the half 504. When engaged, the ring-structure is in a closed and locked position. To release the releasable connection portion 500, a force is applied to a handle 510 adjacent to the slot 508 to widen the slot 508 to allow the protrusion 506 to disengage from the slot 508.

FIGS. 6A-6D depict an alternative embodiment of a connector assembly 600 that may be used to connect or couple the first tubular conduit portion 110 and the second tubular conduit portion 120. The connector assembly 600 includes a first portion 602 and a second portion 604. The first portion 602 may include barbs 124 to irremovably connect the first tubular conduit 110 or the second tubular conduit 120 to the connector assembly 600. In the embodiment shown in FIGS. 6A-6D, an inner surface of the first tubular conduit 110 is engaged with the barbs 124. Another protrusion 606 may be provided on the second portion 604 of the connector assembly 600. The second tubular conduit 120 is disposed over the second portion 604 of the connector assembly 600.

The connector assembly 600 includes a ring structure 608 that extends radially outwardly from a surface of the connector assembly 600. The ring structure 608 may include one or more holes 610. When the second tubular conduit 120 is disposed over the second portion 604, one or more sutures 612 may be threaded through the second tubular conduit 120 and tied to one or more holes 610 of the ring structure 608. To remove the second tubular conduit 120 from the connector assembly 600, the one or more sutures 612 may be cut and the second tubular conduit 120 may be removed from the connector assembly 600 without damage to the second tubular conduit. Although a ring structure 608 is shown in FIGS. 6A-6D, one of ordinary skill in the art will recognize that any structure that extends outwardly from the surface of the connector assembly 600 may be used to tie the suture 612. For example, a single post with a hole may be used.

Figure 7:
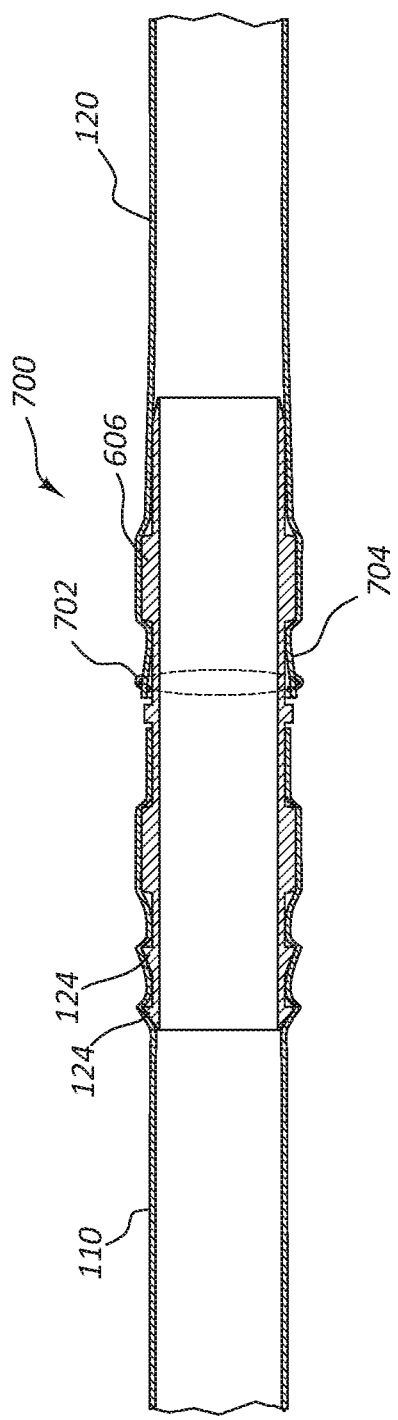
FIG. 7 depicts an alternative embodiment of a connector assembly for the vascular access system.

FIG. 7 shows a cross-section view of another example of a connector 700 according to some embodiments of the disclosure. Connector 700 is similar to connector assembly 600 and so like components are not discussed further. Rather than containing a structure that extends outwardly from the surface of the connector 700, a suture 702 may be tied in a connector area 704 to prevent the second tubular conduit 120 from being removed from the second portion 604. The protrusion 606 along with the suture 704 keep a fluid-tight connection between the first tubular conduit 110 and the second tubular conduit 120. To remove the second tubular conduit 120, the suture 702 may be cut. To then recouple the second tubular conduit 120 to the connector 700, another suture 702 may be used to couple the second tubular conduit 120 to the connector 700. Although a suture 702 is discussed and shown, other connectors may be used, such as a zip tie structure, or either one of releasable connection portions 202 and 500.

Figure 8A:
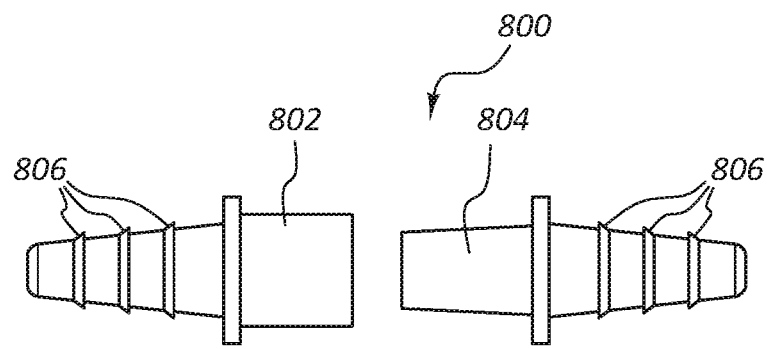
FIG. 8A depicts a side view of a decoupled alternative connector for the vascular access system.
Figure 8B:
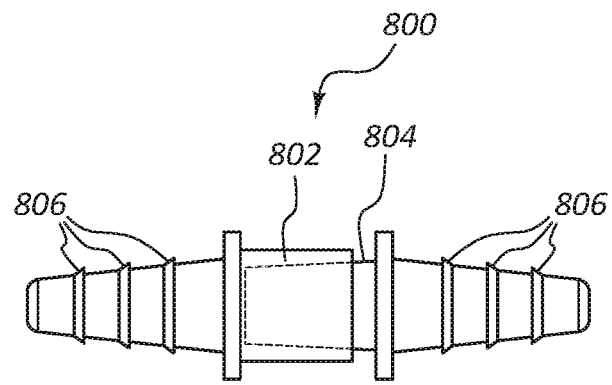
FIG. 8B depicts a side view of the connector of FIG. 8A coupled.

FIGS. 8A-8B illustrate another connector assembly 800 that may be used to releasably connect the first tubular conduit 110 and the second tubular conduit 120. The connector assembly may contain a first member 802 and a second member 804. Each of the first member 802 and the second member 804 may include one or more barbs or protrusions 806, similar to protrusions 124 discussed above. For example, the barbs 806 engage with an inner surface of either the first tubular conduit 110 or the second tubular conduit 120.

Figure 6B:
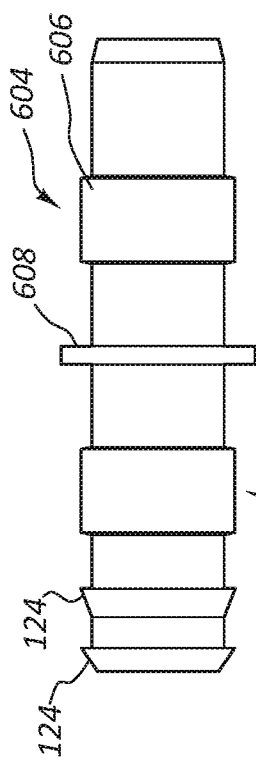
FIG. 6B depicts a side view of the connector assembly of FIG. 6A.
Figure 6C:
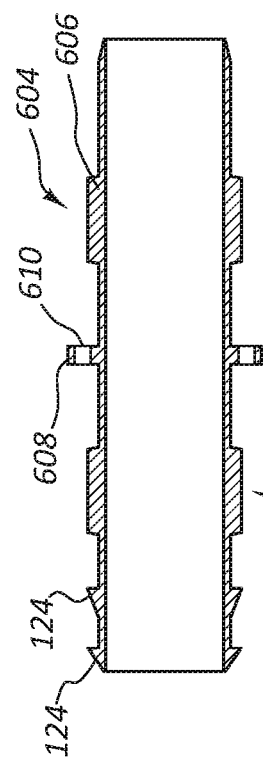
FIG. 6C depicts a cross-sectional view of the connector assembly of FIG. 6A.
Figure 6A:
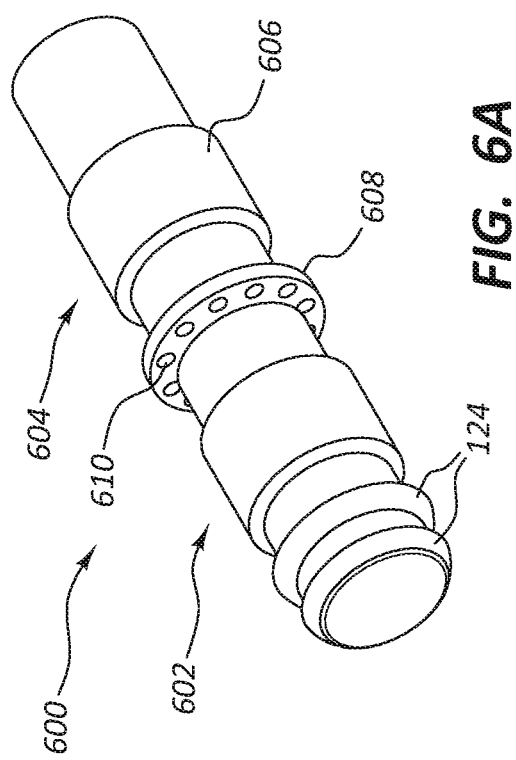
FIG. 6A depicts a perspective view of an alternative embodiment of a connector assembly for the vascular access system.
Figure 6D:
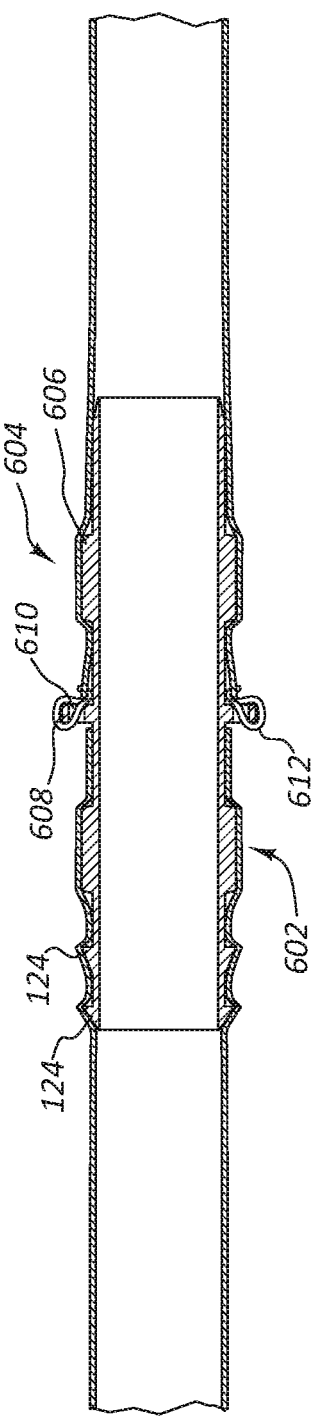
FIG. 6D depicts a cross-sectional view of the connector assembly of FIG. 6A engaged with tubular conduits of the vascular access system.

One member of the first member 802 and the second member 804 is sized to fit within the other member. For example, as seen in FIGS. 6A-6C, an end portion of the second member 804 is sized to fit within an end of the first member 802.

Figure 8C:
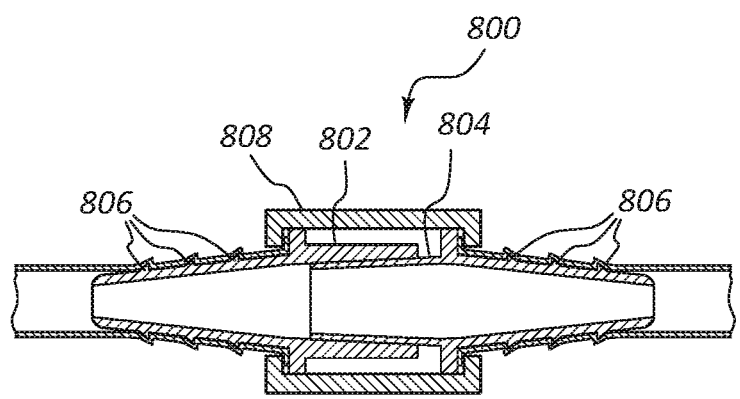
FIG. 8C depicts a cross-sectional view of the connector of FIG. 8A engaged with tubular conduits of the vascular access system.

In FIG. 8C, an inner surface of the first conduit member 110 is engaged with the barbs 806 on the first member 802 and an inner surface of the second conduit member 120 is engaged with the barbs 806 on the second member 804. Similar to barbs 124, any attempt to remove the first tubular conduit 110 from the first member 802 may cause the first tubular conduit 110 to "neck down" or become narrower in diameter, thereby causing the first tubular conduit 110 to more tightly engage with the first member 802. The second tubular conduit 120 and the second member 804 are similarly engaged.

To couple the first tubular conduit 110 and the second tubular conduit 120, the end of the second member 804 is engaged with an end of the first member 802. A clamp 808 may then be provided to provide a force between a neck portion 810 of the first member 802 and a neck portion 812 of the second member 804. This prevents the first tubular conduit 110 and the second tubular conduit 120 from separating while implanted and creates a fluid-tighter connection.

Figure 9:
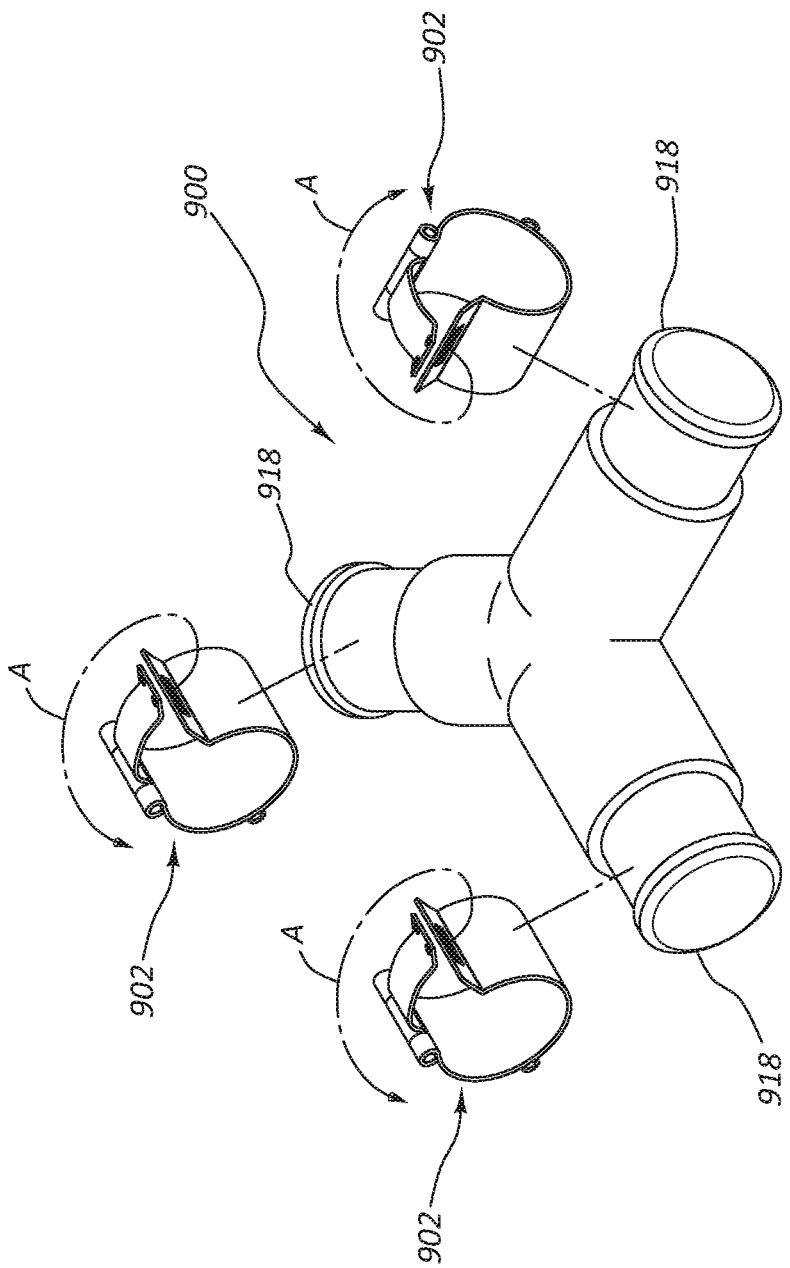
FIG. 9 is another embodiment of a connector.

Although the connectors in FIGS. 3-80 connect to two conduits, it would be apparent to one skilled in the art that a connector may connect to more than two conduits. For example, in some embodiments such as shown in FIG. 9, the connector 900 may be a T or Y shaped connector to releasably connect to three conduits. In other embodiments, the connector may releasably connect to more than three conduits. That is, in each of the embodiments shown in FIGS. 3-8C, the connector may be structured to releasably connect two or more conduits. In some embodiments where the connector connects to three or more conduits, the connector is releasably connected to only some of the conduits.

A T or Y shaped connector, such as connector 900 of FIG. 9, may be utilized in a debranching procedure of the aorta, as it provides a quick connection between multiple different conduits which may be anastomosed to multiple vessels. A debranching procedure is often performed when an aneurysm or other pathology necessitates bypass of a section of the aorta with multiple large arterial branches, such as the renal or mesenteric arteries. The physician will bypass the entire segment of the aorta and create multiple bypass grafts leading to the end organs that are normally fed by this segment of the aorta. In this manner a connector like 900 can provide additional manners of connecting artificial conduits with vessels, and provide a way for the end user to attach and detach these conduits to the vessels. The embodiment of FIG. 9, analogous to the embodiment of FIG. 4A, comprises releasable connection portions 902 locks into position over releasable connector areas 918. The locking systems or mechanisms of any embodiments described herein may be configured for use with a T or Y shaped connector.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified.

Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

The invention claimed is:

1. A vascular access system, comprising:
    a first tubular conduit having a central end portion coupled to a body lumen of a patient and a peripheral end portion;
    a second tubular conduit having a peripheral end portion coupled to a vessel of the patient and a central end portion; and
    a releasable connector having at least a first portion and a second portion, the first portion coupled to the peripheral end portion of the first tubular conduit and the second portion coupled to the central end portion of the second tubular conduit, such that when the first portion and the second portion of the releasable connector are coupled a flow path extends from the vessel to the body lumen via the first and second tubular conduits,
    wherein the releasable connector is configured to decouple from at least one of the first tubular conduit and the second tubular conduit,
    wherein the releasable connector comprises a ring structure extending radially outward from the exterior surface of the releasable connector and includes one or more holes spaced radially apart and configured for tying a suture to one of the holes of the releasable connector.

2. The vascular access system of claim 1, wherein the releasable connector is configured to recouple the first portion to the first tubular conduit and the second portion to the second tubular conduit after decoupling the first portion from the first tubular conduit and the second portion from the second tubular conduit.

3. The vascular access system of claim 1, wherein the first tubular conduit is resistant to kinking and/or crush forces.

4. The vascular access system of claim 1, wherein the releasable connector comprises at least one connector area where a suture is configured to couple at least one of said tubular conduits to the releasable connector.

5. A vascular access system, comprising:
    a first tubular conduit having a central end portion coupled to a body lumen of a patient and a peripheral end portion;
    a second tubular conduit having a peripheral end portion coupled to a vessel of the patient and a central end portion;
    a releasable connector having at least a first portion and a second portion, the first portion coupled to the peripheral end portion of the first tubular conduit and the second portion coupled to the central end portion of the second tubular conduit, such that when the first portion and the second portion of the releasable connector are coupled a flow path extends from the vessel to the body lumen via the first and second tubular conduits; and
    a releasable connection portion that includes a first portion and a second portion connected via a hinge and comprises an open configuration and a locked configured,
    wherein in the locked configuration, the first portion and the second portion form a ring to secure the first tubular conduit or the second tubular conduit to the releasable connector by encircling the first tubular conduit or the second tubular conduit and the releasable connector, and
    wherein the first portion and the second portion are each releasable independent of the other.

6. The vascular access system of claim 5, wherein the releasable connector is configured to recouple the first portion to the first tubular conduit and the second portion to the second tubular conduit after decoupling the first portion from the first tubular conduit and the second portion from the second tubular conduit.

7. The vascular access system of claim 5, wherein the first tubular conduit is resistant to kinking and/or crush forces.

8. The vascular access system of claim 5, wherein the releasable connector comprises a structure extending outwardly from the exterior surface of the releasable connector configured for tying a suture to the releasable connector.

9. The vascular access system of claim 5, wherein the releasable connector comprises at least one connector area where a suture is configured to couple at least one of said tubular conduits to the releasable connector.

* * * * *